Figure 1:
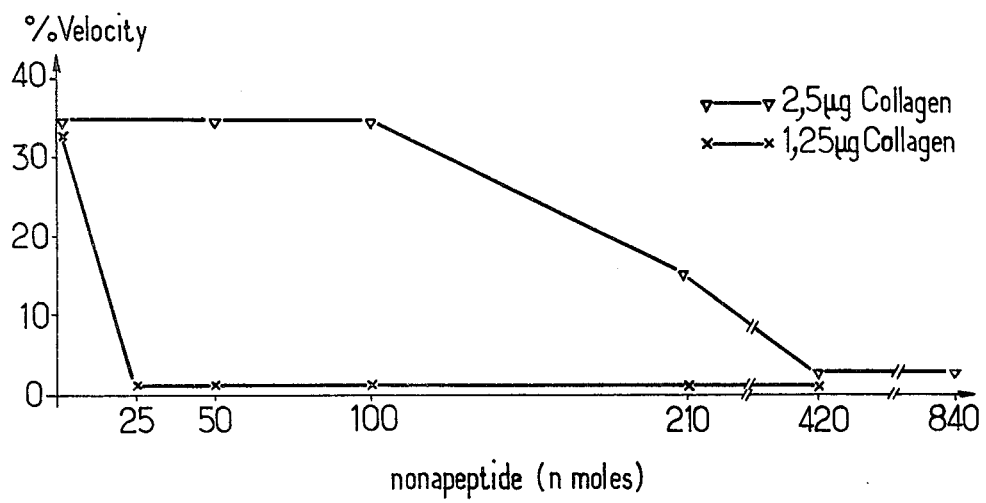

United States Patent [19]

Caen et al.

[11] Patent Number: 4,474,761

[45] Date of Patent: Oct. 2, 1984

[54] OLIGOPEPTIDES WITH SPECIFIC INHIBITING PROPERTIES OF COLLAGEN INDUCED AGGREGATION, PROCESS FOR PREPARING THE SAME AND PHARMACEUTICAL COMPOSITIONS CONTAINING THEM

[75] Inventors: Jacques Caen; Yves Legrand, both of Paris; Pierre Lefrancier, Gif sur Yvette, all of France

[73] Assignee: Choay S.A., Paris, France

[21] Appl. No.: 339,437

[22] PCT Filed: May 11, 1981

[86] PCT No.: PCT/EP81/00046

§ 371 Date: Dec. 26, 1981

§ 102(e) Date: Dec. 26, 1981

[87] PCT Pub. No.: WO81/03329

PCT Pub. Date: Nov. 26, 1981

[30] Foreign Application Priority Data

May 12, 1980 [GB] United Kingdom ................. 8015662

[51] Int. Cl.³ ..................... A61K 37/00; C07C 103/52
[52] U.S. Cl. .............................. 424/177; 260/112.5 R
[58] Field of Search .................. 260/112.5 R; 424/177

[56] References Cited

FOREIGN PATENT DOCUMENTS 5046656 8/1973 Japan ........................... 260/112.5 R

OTHER PUBLICATIONS

J. M. Seyer, et al., Biochemistry 16, No. 6, (1977), 1158–1164.
Chem. Abstr. vol. 92, 1980, 55858r.
Chem. Abstr. vol. 92, 1980, 144153z.
The Journal of Biological Chemistry 250, No. 13, 5076–5081, 1975.
Biochemistry 1981, 20, 2621–2627.
Biochem. & Biophys. Research Commun., 1579–1585, 96, (1980).
The Journal of Biological Chem. 250, 1975, 7428–7434.
Biochemistry 10, (1971), 2076–2081.
C. R. Acad. Sc. Paris 4290, (Apr. 28, 1980), Série D, 1115–1118.

*Primary Examiner*—Delbert R. Phillips
*Attorney, Agent, or Firm*—Weiser & Stapler

[57] ABSTRACT

Oligopeptides having no more than 10 amino acids containing the sequence

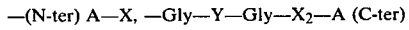

—(N-ter) A—X, —Gly—Y—Gly—$X_2$—A (C-ter)

having the capacity of interacting with blood platelets and an ability to inhibit the aggregation of platelets induced by a collogen containing substance.

11 Claims, 2 Drawing Figures

OLIGOPEPTIDES WITH SPECIFIC INHIBITING PROPERTIES OF COLLAGEN INDUCED AGGREGATION, PROCESS FOR PREPARING THE SAME AND PHARMACEUTICAL COMPOSITIONS CONTAINING THEM

The invention relates to new peptides having biological properties, particularly a capacity of interacting with blood platelets and an ability to inhibit the aggregation of platelets induced by collagen or collagen containing substances.

It also relates to processes for preparing said peptides and lastly to pharmaceutical compositions containing them.

It is known that the vessel wall plays an important role in the maintenance of balance between haemmorrhage and thrombosis. The endothelial lining is thromboresistant, while the subendothelium is thrombogenic.

If the endothelium is pathologically or experimentally damaged, adhesion of the blood platelets to the subendothelial surfaces becomes possible.

The subendothelium comprises different constituents among which can be cited collagen, microfibrils, elastin, etc.

Studies have shown that notably subendothelial collagens and microfibrils are potent inducers of platelet adhesion, which adhesion is responsible for cellular activation with the release of numerous intraplatelet constituents, such as serotonin, and the involvement of many complex biochemical phenomena, which ultimately lead to the aggregation of the platelets.

All these mechanisms are so far but little known.

It is not known in particular which portion of subendothelial collagen, preferably of type III collagen is responsible for platelet adhesion and for the resulting subsequent platelet aggregation.

Recent studies have shown that a 149 aminoacid peptide (hereafter called $\alpha_1(III)CB4$) obtained by enzymatic cleavage of type III collagen, seems responsible for platelet adhesion, whereas the other derived peptidic fragments, resulting from the same enzymatic cleavage, are inactive as regards platelet adhesion (FAUVEL et al. Thrombosis Research, vol. 12, no. 5, p. 841-850).

Further studies and experiments on $\alpha_1(III)CB4$ peptide have been carried out $\alpha_1(III)CB4$ peptide was cleaved by chymotrypsin, hydroxylamin and trypsin to give three fragments, respectively designated as C2 (located between the 63rd and 149th aminoacyl residue of $\alpha_1(III)CB4$), and HA4 (located between the 76th and 149th aminoacyl residue of $\alpha_1(III)CB4$), and T6 (located between the 52nd and 84th aminoacyl residue of $\alpha_1(III)CB4$) (FAUVEL et al., Thrombosis Research, 16, p. 269-273).

The three peptidic fragments have been found to be active as regards platelet adhesion, and the attendant intracellular modification of the metabolism as well as release of intraplatelet constituents, particularly serotonin. A non isolated sequence:

—Gly—Lys—Hyp—Gly—Glu—Hyp—Gly—Pro—Lys— common to the abovesaid peptide fragments C2, HA4 and T6, was considered as possibly representing the "adhesive site" of collagen towards platelets.

It was however found subsequently that the above adhesion active fragments inhibit the aggregation of platelets induced by the type III collagen molecule (FAUVEL et al. Thrombosis Research, 17, p. 285-287) thereby making any prevision on any possible relationship between adhesion and aggregation virtually impossible.

Applicants have now synthesized much smaller peptides, including a nonapeptide including the nine aminoacyl residues defined hereabove in the same order, which have unexpectedly been found to selectively inhibit the aggregation of platelets induced by collagen, yet while being free of the major phenomena that are consequent to adhesion, that is cellular activation and the attendant liberation of platelet constituents.

These small peptides are the first compounds that have been found to inhibit the aggregation of blood platelets as induced by collagen, yet without modifying the natural intracellular metabolism of the platelets, without causing cellular activation and liberation of intraplatelet constituents.

In addition, these peptides specifically inhibiting the interaction between platelet and collagen, are specific inhibitors of platelet aggregation induced by collagen with, suprisingly, no activity against the aggregation induced by other platelet aggregation inducers.

An object of the invention is to provide peptides enabling the minimum sequence of collagen which specifically inhibits the collagen interaction with platelets to be identified.

Another object of the invention is to provide peptides enabling to understand and regulate the platelet aggregation phenomena, with respect to collagen III, in the absence of modification of the natural intracellular metabolism of the platelets and without liberation of intraplatelet constituents, such as serotonin.

A further object of the invention is also to provide peptide reagents, as a means of identification of the minimum sequence of the microfibrils, of any kind of collagen such as those of type I, IV and V, and of any collagen-containing substances which specifically inhibit the collagen interaction with platelet.

Still another object of the invention is to provide new peptides for the production of pharmaceutical drug compositions, effective as platelet aggregation inhibitors useful in particular for the prevention of thrombosis and microthrombosis caused by the injury of the vessel wall.

Particularly it is an object of the invention to provide an active principle for drug compositions, effective as a specific inhibitor of blood platelet aggregation induced by collagen, yet without substantially interfering with the cellular metabolism of said platelets, particularly without causing release of intraplatelet constituents, particularly serotonin or other platelet constituents liable of possessing themselves undesirable side effects.

Thus the invention aims at providing a method for the control of platelet aggregation, more simple to bring into practice in as much as it does not simultaneously involve the control of the side effects caused by the concommittent effects of other drugs used as platelet aggregation inhibitors on the platelet intracellular metabolism.

The invention is relative, in its broadest aspect to peptides containing no more than 10 amino acids, preferably levorotatory amino-acids, and containing the following sequence:

—(N—ter)A—X₁—Gly—Y—Gly—X₂—A(-C—ter)— in which:
X₁ and X₂ represent, independently from each other, either a hydroxyprolyl or a prolyl residue;
Y represents either a —Z—X₃— or a —X₃—X— residue wherein X₃ is a hydroxyprolyl or prolyl residue and Z is a spacer aminoacyl residue and
A is a polyamino-acyl residue, particularly selected from among arginyl, ornithyl or cystyl, preferably however lysyl residues.

As indicated hereabove Z appears essentially to act, together with the X₃ aminoacyl residue, as a "spacer" between the —A—X₁—Gly— and the —Gly—X₂—A peptidyl moieties. Advantageously Z is selected from among dicarboxylic monoamino-acids or monocarboxylic-mono-amino-acids.

Examples of such monocarboxylic-mono-aminoacyl residues are alanyl, leucyl, isoleucyl, norleucyl, valyl, glycyl, prolyl. Preferably however Z is selected from among glutaminyl, glutamyl, aspartyl and asparaginyl.

In a preferred class of compounds of the invention, one at least of the A terminal residue is engaged in a peptitic bond with a glycyl residue.

In another preferred class of compounds of the invention, the N-terminal residue A is a lysyl residue, possibly itself engaged in a peptidic bond with a glycyl residue.

In another preferred class of compounds of the invention, the C-terminal residue is a lysyl residue, possibly itself engaged in a peptitic bond with a glycyl residue.

A particular preferred class of compounds of the invention contains a sequence having the following formula:

—(N—ter)A—X₁—Gly—Z—X₃—Gly—X₂—A(-C—ter)— in which:
A represents a residue chosen from the following: lysyl, arginyl,
X₁, X₂ and X₃ represent independently from each other either the hydroxyprolyl residue, or the prolyl residue;
Z is selected from among dicarboxylic monoaminoacids or monocarboxylic monoaminoacids, and is preferably chosen among glutaminyl, glutamyl, aspartyl and asparaginyl.

Another preferred class of compounds according to the invention, contains a peptidic sequence having the following formula:

—(N—ter)A—X₁—Gly—X₃—Z—Gly—X₂—A(-C—ter)— in which:
A, X₁, X₂, X₃ and Z have the above meanings.

In preferred compounds of the invention, Z is a glutamyl residue, the formulae of the corresponding peptides then containing either of the following sequences:

—(N—ter)A—X₁—Gly—Glu—X₃—Gly—X₂—A(-C—ter)—

—(N—ter)A—X₁—Gly—X₃—Glu—Gly—X₂—A(-C—ter)— in which:
A, X₁, X₂ and X₃ have the above mentioned meanings.

In further preferred compounds of the invention, A represents the lysyl residue, the formulae of the corresponding peptides then containing either of the following sequences:

—(N—ter)Lys—X₁—Gly—Glu—X₃—Gly—X₂—Lys(C—ter)—

—(N—ter)Lys—X₁—Gly—X₃—Glu—Gly—X₂—Lys(C—ter)— in which:
X₁, X₂ and X₃ represent independently from each other either the hydroxyprolyl residue, or the prolyl residue.

In orther preferred compounds of the invention, X₁, X₂ and X₃ simultaneously represent the prolyl residue.

In other preferred compounds of the invention, X₁, X₂ and X₃ simultaneously represent the hydroxyprolyl residue.

In other preferred compounds of the invention, X₁ represents the hydroxyprolyl residue and X₂ the prolyl residue or vice-versa.

In other preferred compounds of the invention, X₁ and X₃ simultaneously represent the hydroxyprolyl residue and X₂ represent the prolyl residue or vice-versa.

Preferred peptides of the invention have the following formula:

Lys—Pro—Gly—Glu—Pro—Gly—Pro—Lys
Lys—Hyp—Gly—Glu—Pro—Gly—Hyp—Lys
Lys—Pro—Gly—Glu—Pro—Gly—Hyp—Lys
Lys—Hyp—Gly—Glu—Pro—Gly—Pro—Lys
Lys—Pro—Gly—Glu—Hyp—Gly—Pro—Lys
Lys—Hyp—Gly—Glu—Hyp—Gly—Hyp—Lys
Lys—Pro—Gly—Glu—Hyp—Gly—Hyp—Lys
Lys—Hyp—Gly—Glu—Hyp—Gly—Pro—Lys
Gly—Lys—Pro—Gly—Glu—Pro—Gly—Pro—Lys (1)
Gly—Lys—Hyp—Gly—Glu—Pro—Gly—Hyp—Lys
Gly—Lys—Pro—Gly—Glu—Pro—Gly—Hyp—Lys
Gly—Lys—Hyp—Gly—Glu—Pro—Gly—Pro—Lys
Gly—Lys—Pro—Gly—Glu—Hyp—Gly—Pro—Lys
Gly—Lys—Hyp—Gly—Glu—Hyp—Gly—Hyp—Lys
Gly—Lys—Pro—Gly—Glu—Hyp—Gly—Hyp—Lys
Gly—Lys—Hyp—Gly—Glu—Hyp—Gly—Pro—Lys (4)
Lys—Pro—Gly—Glu—Pro—Gly—Pro—Lys—Gly
Lys—Hyp—Gly—Glu—Pro—Gly—Hyp—Lys—Gly
Lys—Pro—Gly—Glu—Pro—Gly—Hyp—Lys—Gly
Lys—Hyp—Gly—Glu—Pro—Gly—Pro—Lys—Gly
Lys—Pro—Gly—Glu—Hyp—Gly—Pro—Lys—Gly
Lys—Hyp—Gly—Glu—Hyp—Gly—Hyp—Lys—Gly
Lys—Pro—Gly—Glu—Hyp—Gly—Hyp—Lys—Gly
Lys—Hyp—Gly—Glu—Hyp—Gly—Pro—Lys—Gly (2)
Tyr—Gly—Lys—Hyp—Gly—Glu—Hyp—Gly—Pro—Lys (3)
Lys—Pro—Gly—Pro—Glu—Gly—Pro—Lys
Lys—Hyp—Gly—Pro—Glu—Gly—Hyp—Lys
Lys—Pro—Gly—Pro—Glu—Gly—Hyp—Lys
Lys—Hyp—Gly—Pro—Glu—Gly—Pro—Lys
Lys—Pro—Gly—Hyp—Glu—Gly—Pro—Lys
Lys—Hyp—Gly—Hyp—Glu—Gly—Hyp—Lys
Lys—Pro—Gly—Hyp—Glu—Gly—Hyp—Lys
Lys—Hyp—Gly—Hyp—Glu—Gly—Pro—Lys
Gly—Lys—Pro—Gly—Pro—Glu—Gly—Pro—Lys
Gly—Lys—Hyp—Gly—Pro—Glu—Gly—Hyp—Lys

Gly—Lys—Pro—Gly—Pro—Glu—Gly—Hyp—Lys
Gly—Lys—Hyp—Gly—Pro—Glu—Gly—Pro—Lys
Gly—Lys—Pro—Gly—Hyp—Glu—Gly—Pro—Lys
Gly—Lys—Hyp—Gly—Hyp—Glu—Gly—Hyp—Lys
Gly—Lys—Pro—Gly—Hyp—Glu—Gly—Hyp—Lys
Gly—Lys—Hyp—Gly—Hyp—Glu—Gly—Pro—Lys
Lys—Pro—Gly—Pro—Glu—Gly—Pro—Lys—Gly
Lys—Hyp—Gly—Pro—Glu—Gly—Hyp—Lys—Gly
Lys—Pro—Gly—Pro—Glu—Gly—Hyp—Lys—Gly
Lys—Hyp—Gly—Pro—Glu—Gly—Pro—Lys—Gly
Lys—Pro—Gly—Hyp—Glu—Gly—Pro—Lys—Gly
Lys—Hyp—Gly—Hyp—Glu—Gly—Hyp—Lys—Gly
Lys—Pro—Gly—Hyp—Glu—Gly—Hyp—Lys—Gly
Lys—Hyp—Gly—Hyp—Glu—Gly—Pro—Lys—Gly
Tyr—Gly—Lys—Hyp—Gly—Hyp—Glu—Gly—Pro—Lys

In an advantageous embodiment of the invention, the peptides have the following formula:

Lys—Pro—Gly—Glu—Pro—Gly—Pro—Lys    (1)

Gly—Lys—Hyp—Gly—Glu—Hyp—Gly—Pro—Lys    (4)

Other features and advantages of the invention will be apparent for those skilled in the art from the following description and the preferred embodiments of the invention.

SYNTHESIS OF PEPTIDES ACCORDING TO THE INVENTION

One may resort to processes conventional per se, for peptide synthesis for producing the peptides according to the invention. They are recalled hereafter briefly.

The synthesis of peptides in homogeneous solution and by solid phase peptide synthesis are well documented (HOUBEN-WEYL "Methoden der Organischen Chemie" E. Wünsch Eds, vol. 15-I et II THIEME, Stuttgart 1974).

Two different approaches are possible in peptide synthesis, that of fragment condensation and stepwise synthesis. Both strategies require that one aminoacid or peptide fragment have its amino group protected and its carboxyl group activated and that the second aminoacid or peptide fragment have its amino group free and its carboxyl group protected; when the aminoacid involved has two amino functions, such as lysine, or two acid functions, such as glutamic acid, it is necessary to protect either the amino function or the acid function not involved in the peptidic synthesis by protecting groups, preferably carbobenzoxy or t-butyloxycarbonyl groups for the amino function, for instance a lysyl residue and t-butylester groups for the acid functions, for instance of a glutamyl residue.

As regards the stepwise synthesis the aminoacids are added one after each other, starting with the C-terminal aminoacid.

As regards the fragment condensation strategy, all the combinations can be theoretically contemplated, provided they do not involve the condensation of a fragment whose C-terminal residue is either lysine or glutamic acid (because of a possible racemisation).

This way is quick, since several fragments can be prepared at the same time, then linked to each other.

Final purifying is made easier because of the difference in the molecular weight between the fragments and the complete peptide chain.

More particularly, in an advantageous embodiment of the invention, the synthesis of the nine aminoacid peptides of the formula (4) according to the invention, is carried out by resorting to fragment condensation, with the synthesis of the three following fragments:

Gly—Lys—Hyp

Gly—Glu—Hyp

Gly—Pro—Lys which enables to have fragments to be coupled whose C-terminal residue is not racemisable.

Convention of designation of the individual aminoacyl residues in different peptide fragments considered hereafter:

Numbers have been specifically assigned to the different aminoacyl residues by reference to the position which they occupy, when contained in the decapeptide of formula:

Gly—Lys—Hyp—Gly—Glu—Hyp—Gly—Pro—Lys—Gly

Thus any of said numbers, when used to designate the aminoacyl residues contained in a smaller peptide fragment merely refers back to the corresponding aminoacyl residue and is not intended to specify the position of the latter with respect to N-terminal residue of said smaller fragment.

SYNTHESIS OF NONAPEPTIDE

Gly—Lys—Hyp—Gly—Glu—Hyp—Gly—Pro—Lys
 1      2     3     4    5     6    7    8    9

In a more preferred embodiment of the invention, the process for preparing the peptidic sequence of formula (4) is carried out as reported below.

In the course of the specification, the abbreviations which are used have the following meaning:

| | |
|---|---|
| Z | carbobenzoxy- |
| BOC | t-butyloxycarbonyl- |
| OMe | methylester |
| OBu$^t$ | t-butylester |
| OSu | succinimid ester |
| Hyp | hydroxyprolin |
| Glu | glutamic acid |
| Pro | prolin |
| Gly | glycin |
| Lys | lysin. |

Chromatographies on thin layer of silica gel have been carried out, in which the solvent mixtures which have been used (v/v) are the following ones:
chloroform-aceton: 5-2 (A)
chloroform-methanol: 8-1 (B), 50-15 (C), 9-1 (D), 6-1 (E)
chloroform-methanol-benzen: 8-1-1 (F)
ethyl acetate-hexane: 9-1 (G)
ethyl acetate-pyridin-acetic acid-water: 6-2-0, 6-1 (H), 12-2-0, 6-1 (I), 5-5-1-3 (J).

The identifications have been carried out with ninhydrine and chlore-o-tolidine reactive.

For the purification, Silica Gel 60 (trademark of resin commercialized by MERCK-Darmstadt, Germany) was used.

The nonapeptide of the following formula (4):

Gly—Lys—Hyp—Gly—Glu—Hyp—Gly—Pro—Lys has been synthesized by means of fragment condensation in which the three following fragments:
Gly—Lys—Hyp—Gly (1-4 fragment),
Glu—Hyp (5-6 fragment),
Gly—Pro—Lys (7-9 fragment),
have been prepared.

SYNTHESIS OF 1-4 FRAGMENT
Z—Gly—Lys—(Z)—Hyp—Gly—OH
BOC—Lys—(Z)—Hyp—OMe (I)

1.43 g (3 mM) of BOC—Lys—(Z)—OSu (P. Hartter, Hoppe Seyler's. Physiol. Chem. 357 (1976), 1 683) dissolved in 5 ml of dimethylformamid are added to a solution, cooled to 0° C., of 363 mg (2 mM) of Hyp—OMe, HCl (E. L. Smith and M. Bergmann, j. Biol. Chem. 153 (1944), 627) and 0.22 ml (2 mM) of N-methylmorpholine in 5 ml of dimethylformamid. The reaction mixture is stirred for a night at ambient temperature then treated with 0.30 ml (3 mM) of dimethylaminopropylamine for one hour. The dimethylformamid is concentrated to dryness and the residue is taken up in 50 ml of ethyl acetate. This organic phase is successively washed with KH SO₄ 5%, in water, with NaHCO₃M, in water then dried over Mg SO₄, and concentrated to dryness. The oil which is obtained (860 mg) is chromatographed on a column (28×3 cm) of silica 60 (89 g), eluted with the solvent mixture of chloroform-aceton 5-2 (v/v).

The fractions are gathered and concentrated to dryness into a residue which is taken up in aceton, ultrafiltrated, concentrated and precipitated in ether-hexan: 675 mg (corresponding to a yield of 66.5%) of compound (I) are obtained.
MP=112° C.
$[\alpha]_D^{20} = -53.8°$ (c=0.5, chloroform)
Rf.=0.28 (A)
Rf.=0.27 (G)

The elementary analysis of the product is:

| $C_{25}H_{37}N_3O_8$ (507.60) | C % | H % | N % |
|---|---|---|---|
| calculated | 59.2 | 7.3 | 8.3 |
| found | 58.6 | 7.3 | 8.0 |

Lys—(Z)—Hyp-OMe, HCl (II)

597 mg (1.17 mM) of compound (I) are treated with 3.6 ml of HCl solution (1N) in acetic acid, for 30 minutes. After concentration, 560 mg of residue are obtained and dried (corresponding to a yield of 100%).
Rf.=0.38 (H)

Z—Gly—Lys—(Z)—Hyp—OMe (III)

460 mg (1.5 mM) of Z—Gly—OSu (G. W. Anderson, J. E. Zimmermann and F. M. Callahan, J. AM. Chem. Soc. 86 (1964) 1 839) dissolved in 5 ml of dimethylformamid are added to a solution which has been cooled to 0° C., of 560 mg (1.1 mM) of compound (II) and 0.16 ml (1.1 mM) of triethylamin in 5 ml of dimethylformamid. The compound (III) is prepared as it has been described for compound (I). The oily residue obtained (742 mg) is chromatographed on column (30×3 cm) of silica 60 (100 g) eluted with a solvent mixture of chloroform methanol 1-1 (v/v). The fractions obtained (533 mg corresponding to a yield of 79%) are treated as usual:

Rf.=0.58 (B)
Rf.=0.39 (E)

Z—Gly—Lys—(Z)—Hyp—OH (IV)

520 mg (0.87 mM) of compound (III) are solubilized in 8.5 ml of absolute methanol and treated for 4 hours with 1 ml of 2M NaOH solution. After addition of 10 ml of water, the methanol is evaporated and the aqueous phase is extracted with ethyl acetate, then acidified with citric acid (pH 3). This aqueous phase is extracted by means of ethyl acetate, then, it is washed with an aqueous solution saturated in NaCl, and it is further dried over MgSO₄ and concentrated to dryness: 390 mg of compound (IV) are obtained, which correspond to a yield of 76.8%.
Rf.=0.18 (I)

Z—Gly—Lys—(Z)—Hyp—Gly—OBuᵗ (V)

117 mg (0.2 mM) of compound (IV) are dissolved in 2 ml of dimethylformamid. 22 μl (0.2 mM) of Gly—O-Buᵗ, HCl (C. H. Li, B. Gorup, D. Chung, and J. Ramachandran, J. Org. Chem. 28 (1963) 178) and 24 μl (0.22 mM) of N-methylmorpholin in 2 ml of dimethylformamid are successively added to this solution cooled to −15° C. After 4 hours, at −15° C., 0.2 ml of a 2.5 MKHCO₃ solution are added to the reaction mixture, then 30 minutes after, 20 ml of ethyl acetate are added. The organic phase is washed with NaHCO₃M, in water, with KHSO₄ 5%, in aqueous solution saturated in NaCl, then it is dried over MgSO₄ and concentrated to dryness (114 mg corresponding to a yield of 103%).
Rf.=0.71 (I)

Z—Gly—Lys—(Z)—Hyp—Gly—OH (VI)

114 mg (0.2 mM) of compound (V) are treated with 0.2 ml of trifluoroacetic acid for 30 minutes. After concentration to dryness, the residue (150 mg) is purified on a column (22×1.5 cm) of silica 60 (20 g), eluted with the solvent mixture: ethyl acetate-pyridin-acetic acid-water 4.5-2-0.6-1 (v/v).

The fractions obtained (112 mg corresponding to a yield of 87.3%) are treated as usual.
Rf.=0.26 (H)

SYNTHESIS OF 5-6 FRAGMENT
Z—Glu—(OBuᵗ)—Hyp—OH
Z—Glu—(OBuᵗ)—Hyp—OMe (VII)

1.3 g (3 mM) of Z—Glu—(OBuᵗ)—OSu (A. Eberlé, J. L. Franchère, G. I. Tesser and R. Schwyzer, Helv. Chim. Acta. 58 (1975) 2 106) dissolved in 5 ml dimethylformamid, are added to a solution cooled to 0° C. of 363 mg (2 mM) of Hyp—OMe, HCl (E. L. Smith and M. Bergmann, J. Biol. Chem. 153 (1944), 627) and 0.22 ml (2 mM) of N-methylmorpholin. Compound (VIII) is prepared as it has been described for compound (I). The oily residue which is obtained (627 mg corresponding to a yield of 68%) is only crystallized in ethyl acetate petroleum ether.
MP=105°-106°
$[\alpha]_D^{20} = -58.5°$ (c=1, glacial acetic acid)
The elementary analysis of the product is:

| $C_{23}H_{32}O_2N_8$ (464.52) | C % | H % | N % |
|---|---|---|---|
| calculated | 59.5 | 6.9 | 6.0 |
| found | 59.2 | 7.0 | 5.8 |

Z—Glu—(OBu$^t$)—Hyp—OH (VIII)

495 mg (1.06 mM) of compound (VII) are solubilized in 10 ml of absolute methanol and treated for 4 hours with 1 ml of 2M KOH. Compound (VIII) is then prepared as it has been described for compound (IV). The oily residue which has been obtained (533 mg) is chromatographed on a column (28×3 cm) of silica 60 (51 g) eluted with a solvent mixture of ethyl acetate pyridine-acetic acid-water 9-2-0.6-1 (v/v). The fractions are treated as usual. The product is crystallized in acetone-petroleum ether; (309.6 mg which correspond to a yield of 65% of compound (VII) are thus obtained.

MP (decomposition)=55°–68°
$[\alpha]_D^{20} = -52.8°$ (c=0.4, chloroform)
Rf.=0.68 (H)
Rf.=0.37 (I)
The elementary analysis of the product is:

| $C_{22}H_{30}N_2O_8$ (452.40) | C % | H % | N % |
|---|---|---|---|
| calculated | 58.7 | 6.7 | 6.2 |
| found | 58.4 | 6.6 | 5.8 |

SYNTHESIS OF 7-9 FRAGMENT
Gly—Pro—Lys—(BOC)—OBu$^t$, acetate Z—Gly—Pro (IX)

1.9 g (6.2 mM) of Z—Gly—OSu (G. W. Anderson, J. E. Zimmermann and F. M. Callahan, J. Am. Chem. Soc. 86 (1964) 1 839) dissolved in 5 ml of tetrahydrofuran are added to a solution cooled to 0° C., of 691 mg (6 mM) of prolin and 505 mg (6 mM) of NaHCO$_3$ in 10 ml of tetrahydrofuran and 5 ml of water. Compound (IX) is prepared as it has been described for compound (I). The oily residue is crystallized without any other purification in ethyl acetate. 1.07 g which correspond to a yield of 58.2% of compound (IX) are obtained.

MP=152°–154°
$[\alpha]_D^{20} = -66.4°$ (c=1 absolute ethanol)
Rf.=0.64 (I)
(Litt. MP=150°–151°)
$[\alpha]_D^{20} = -60°$ (absolute ethanol)

Z—Gly—Pro—Lys—(BOC)—OBu$^t$ (X)

1.053 g (3.44 mM) of compound (IX) are dissolved in 10 ml of dimethylformamid. 0.38 ml (3.54 mM) of N-methylmorpholin and 0.45 ml (3.45 mM) of isobutyl chlorocarbonate are added to this solution cooled to −15° C., 3 minutes after, a cooled solution of 1.25 g (3.44 mM) of Lys—(BOC)—OBu$^t$, acetate and 0.38 ml (3.45 mM) of N-methylmorpholin in 10 ml of dimethylformamid is added. Compound (X) is prepared as it has been described for compound (V). The residue which is obtained (2 g) is purified on a silica column (designated under Chromatospack, manufactured by Jobin and Yvon, France) eluted with a solvent mixture chloroform-aceton 50-15 (v/v). The fractions are treated as usual. The product is crystallized in aceton-ether-hexan. 1.435 g of compound (X) (which correspond to a yield of 70.7%) are thus obtained.

Rf.=0.33 (C)
Rf.=0.32 (G)

Gly—Pro—Lys—(BOC)—OBu$^t$, acetate (XI)

1.435 g (2.43 mM) of compound (X) are solubilized in 20 ml of glacial acetic acid and hydrogenated for 4 hours with palladium 5% on coal. After filtration on the catalyst, the filtrate is concentrated to dryness and the residue is dried. 1.4 g of compound (XI) (which correspond to a yield of 100%) are thus obtained.

Rf.=0.28 (H)

SYNTHESIS OF 5-9 FRAGMENT
Glu—(OBu$^t$)—Hyp—Gly—Pro—Lys—(BOC)—OBu$^t$

Z—Glu—(OBu$^t$)—Hyp—Gly—Pro—Lys—(BOC)—OBu$^t$ (XII)

288 mg (0.64 mM) of compound (VIII) are dissolved into 3 ml of dimethylformamid. 70 μl (0.64 mM) of N-methylmorpholin and 83 μl (0.64 mM) of isobutyl chlorocarbonate are successively added to this solution cooled to −15° C. 3 minutes after, a cooled solution of 440 mg (0.85 mM) of compound (XI) and 94 μl (0.85 mM) of N-methylmorpholin in 5 ml of dimethylformamid are added. Compound (XII) is prepared as it has been described for compound (V). The residue which is obtained (545 mg) is purified on a column (30×3 cm) of silica 60 (100 g), eluted with the solvent mixture: chloroform-methanol 9-1 (v/v). The fractions which are obtained (450 mg corresponding to a yield of 54%) are treated as usual.

Rf.=0.64 (I)
Rf.=0.40 (D)

Glu—(OBu$^t$)—Hyp—Gly—Pro—Lys—(BOC)—OBu$^t$, acetate (XIII)

450 mg (0.5 mM) of compound (XII) are solubilized in 40 ml of acetic acid and hydrogenated for 4 hours with palladium 5% on coal. After filtration of the catalyst, the filtrate is concentrated to dryness. 408 mg of compound (XIII) (which correspond to a yield of 100%) are thus obtained.

Rf.=0.54 (H)

SYNTHESIS OF 1-9 FRAGMENT
Gly—Lys—Hyp—Gly—Glu—Hyp—Gly—Pro—Lys

Z—Gly—Lys—(Z)—Hyp—Gly—Glu—(OBu$^t$)—Hyp—Gly—Pro—Lys—(BOC)—OBu$^t$ (XIV)

112 mg (0.17 mM) of compound (VI) are dissolved in 2 ml of dimethylformamid. 19 μl (0.17 mM) of N-methylmorpholin and 22 μl (0.17 mM) of isobutyl chlorocarbonate are successively added to this solution cooled to −15° C. 3 minutes after, a cooled solution of 169 mg (0.2 mM) of compound (XIII) and 22 μl (0.2 mM) of N-methylmorpholin in 5 ml of dimethylformamid are added. Compound (XIV) is prepared as it has been described for compound (V). The residue which is obtained (224 mg) is solubilized in chloroform and chromatographied on a column (22×1.5 cm) of silica 60 (20 g), eluted with a solvent mixture, chloroform-methanol 6-1 (v/v). The fractions obtained (53 mg) are treated as usual. The non pure fractions obtained (135 mg) are gathered and concentrated. This raw product is purified on a column (15×1.5 cm) of silica 60 (13 g), eluted successively with the following solvent mixtures: chloroform-methanol 10-1, 8-1, 7-1 and 6-1 (v/v). The fractions obtained (66 mg) are treated as usual.

Rf.=0.32 (E)

Gly—Lys—Hyp—Gly—Glu—Hyp—Gly—Pro—Lys (XV) (4)

53 mg (38.4 mM) of compound (XIV) are treated for 30 minutes with 1 ml of trifluoroacetic acid. After concentration to dryness, the residue is dissolved in 5 ml of acetic acid and hydrogenated for 2 hours with palladium 5% on coal. After filtration of the catalyst, the filtrate is concentrated to dryness. The residue is taken up in water, ultrafiltrated, then lyophilized. 39.6 mg of compound (4) (corresponding to a yield of 91%) are thus obtained.

$|\alpha|_D^{20} = -73.6°$ (H$_2$O)
Rf.=0.08 (J)

The nonapeptide was obtained in the form of its trifluoroacetic salt in association with water molecules.

The elementary analysis of the product is:

| C$_{38}$H$_{63}$N$_{11}$O$_{14}$; 2.5 CF$_3$COOH; 1.5 H$_2$O (1 210,05) | | | |
|---|---|---|---|
| | C % | H % | N % |
| calculated | 42.7 | 5.7 | 12.7 |
| found | 42.10 | 5.6 | 12.5 |

The nonapeptide can be obtained without water molecules, according to classical methods.

The elementary analysis of the nonapeptide free from water is the following one:

| C$_{38}$H$_{63}$N$_{11}$O$_{14}$; 2.5 CF$_3$COOH | | | |
|---|---|---|---|
| | C % | H % | N % |
| calculated | 43.65 | 5.58 | 13.02 |
| found | 43.2 | 5.6 | 12.09 |

The aminoacid analysis after total acid hydrolysis gives the following results:

| (HCl 6N - 110° | -Gly (3), 3.0-Lys (2) 2.0 |
|---|---|
| | -Pro (1), 1.1-Glu (1), 1.0-Hyp (2) 2.0 |

The nonapeptide can be obtained free from anion according to conventional methods of chromatography on ion exchange resins.

The nonapeptide can also be obtained in the form of any of its mineral or organic salts such as in the form of chlorhydrate, acetate, picrate, paratoluenesulfonate, according to classical methods of ion exchange.

The preferred salts of the nonapeptide are those which are physiologically acceptable such as the acetate salt.

The nonapeptide is obtained in the form of its acetate by chromatography of compound (XV) on a resin such as the one known under the designation "Amberlite IRA 45" commercialized by BIORAD Laboratories.

The fragment condensation (in the choice of the peptidic fragments which are first synthesized and then condensed) which has been carried out to obtain peptide of formula (4) can be explained as follows.

PREPARATION OF 5-9 FRAGMENT

Document of the prior art (E. Adams, Synthesis and Derivatives of 3-and 4-hydroxyproline, Int. J. Peptide Protein Res. 8 (1976) 503), relates to some of the difficulties in the preparation of peptides of sequence:

Glu—Hyp.

Accordingly, no result being obtained in the condensation of:

BOC—Glu—(Obu$^t$)—OSu with H—Hyp—OH
(corresponding to 5-6 fragment)

the synthesis of:

Z—Glu—(OBu$^t$)—Hyp—OH      (VIII)

has been carried out as follows:

Z—Glu—(OBu$^t$)—OSu + H—Hyp—OMe
↓
Z—Glu—(OBu$^t$)—Hyp—OMe      (VII)
↓
Z—Glu—(OBu$^t$)—Hyp—OH      (VIII)

(VIII) has been linked with the 7-9 fragment, which has been previously synthesized and whose protective groups have been imposed, as to their type, by the one of 5-6 fragment:

Z—Gly—Pro—Lys—(BOC)—OBu$^t$      (X)
↓
H—Gly—Pro—Lys—(BOC)—OBu$^t$      (XI)

5-9 fragment was thus obtained:

Z—Glu—(OBu$^t$)—Hyp—Gly—Pro—Lys—(BOC)—OBu$^t$      (XII)
↓
H—Glu—(OBu$^t$)—Hyp—Gly—Pro—Lys—(BOC)—OBu$^t$      (XIII)

(VIII) could also have been readily linked after elimination of Z group, with Z—Gly—OSu, to obtain Z—Gly—Glu—(OBu$^t$)—Hyp—OMe.

4-6 fragment could have been increased either on the C-terminal side (after saponification) either on the N-terminal side (after eliminating the Z group).

PREPARATION OF 1-4 FRAGMENT

The following dipeptide:

(BOC)—Lys—(Z)—Hyp—OMe      (I)

has firstly been prepared, then after eliminating the BOC group, has been condensed to:
Z—Gly—OSu which gave:

Z—Gly—Lys—(Z)—Hyp—OMe      (III)
↓
Z—Gly—Lys—(Z)—Hyp—OH      (IV)

This (IV) fragment could have been linked to 4-6 fragment. But it has preferably been linked to glycine as follows:

Z—Gly—Lys—(Z)—Hyp—Gly—OBu$^t$
↓

-continued
Z—Gly—Lys—(Z)—Hyp—Gly—OH

The OBu<sup>t</sup> ester has been advantageously used (rather than OMe ester) because the saponification of the latter is rather difficult.

The nonapeptide was obtained as follows:

Z—Gly—(Z)—Hyp—Gly—Glu—(OBu<sup>t</sup>)—Hyp—Gly—Pro—Lys—(BOC)OBu<sup>t</sup>   (XIV)
↓
Z—Gly—Lys—(Z)—Hyp—Gly—Glu—Hyp—Gly—Pro—Lys
↓
Gly—Lys—Hyp—Gly—Glu—Hyp—Gly—Pro—Lys One may add that the fact to protect, as regards 1-4 fragment, the amino functions by hydrogenolysable groups (Z) rather than acidolysable (BOC), takes into account the obtention of the:

Z—Gly—Lys—(Z)—Hyp—Gly—Glu—Hyp—Gly—Pro—Lys partially deprotected, and which can be easily purified because of its intermediary polarity as regards nonapeptide derivatives (XIV) and (XV).

It must be pointed out that the linking of the three contemplated fragments could have been carried out in an other order without any problem. The tactic choices could have possibly been different.

SYNTHESIS OF OCTAPEPTIDE

Lys—Hyp—Gly—Glu—Hyp—Gly—Pro—Lys
 2    3    4    5    6    7    8    9

In order to obtain said octapeptide, recourse is had to fragment condensation as follows:
synthesis of 2-4 fragment,
synthesis of 5-9 fragment,
condensing 2-4 fragment with 5-9 fragment.

SYNTHESIS OF Lys—Hyp—Gly (2-4 fragment)

This synthesis is carried out according to the following reaction diagram:

BOC—Lys—(Z)—Hyp—OMe
↓
BOC—Lys—(Z)—Hyp—OH
↓
BOC—Lys—(Z)—Hyp—Gly—OBu<sup>t</sup>
↓
BOC—Lys—(Z)—Hyp—Gly—OH (XV) (4)

BOC—Lys—(Z)—Hyp—OH is prepared from BOC—Lys—(Z)—Hyp—OMe according to the same reaction as the one involved for the synthesis of compound (IV) obtained from compound (III) (preparation of 1-4 fragment of nonapeptide of formula (XV) (4).

BOC—Lys—(Z)—Hyp—Gly—OBu<sup>5</sup> is prepared from BOC—Lys—(Z)—Hyp—OH according to the same reaction as the one involved for the synthesis of compound (V) obtained from compound (IV) (preparation of 1-4 fragment of nonapeptide of formula (XV) (4).

BOC—Lys—(Z)—Hyp—Gly—OH is prepared from BOC—Lys—(Z)—Hyp—Gly—OBu<sup>t</sup> according to the same reaction as the one involved for the synthesis of compound (VI) obtained from compound (V) (preparation of 1-4 fragment of nonapeptide of formula (XV) (4).

SYNTHESIS OF Glu—Hyp—Gly—Pro—Lys (5-9 fragment)

The preparation of this fragment is carried out as it has been described in the preparation of nonapeptide of formula (XV) (4).

SYNTHESIS OF Lys—Hyp—Gly—Glu—Hyp—Gly—Pro—Lys (2-9 fragment)

The octapeptide 2-9 is obtained as follows: (involving the same reactions as the one described for the synthesis of nonapeptide of formula (XV) (4):

BOC—Lys—(Z)—Hyp—Gly—OH + H—Glu—(OBu<sup>t</sup>)—Hyp—Gly—Pro—Lys—(BOC)—OBu<sup>t</sup> ⟶

BOC—Lys—(Z)—Hyp—Gly—Glu—(OBu<sup>t</sup>)—Hyp—Gly—Pro—Lys—(BOC)—OBu<sup>t</sup> ⟶

Lys—Hyp—Gly—Glu—Hyp—Gly—Pro—Lys

SYNTHESIS OF NONAPEPTIDE

Lys—Hyp—Gly—Glu—Hyp—Gly—Pro—Lys—Gly
 2    3    4    5    6    7    8    9   10

Recourse is had to the fragment condensation as follows:
synthesis of 2-4 fragment,
synthesis of 5-6 fragment,
synthesis of 7-10 fragment,
condensing 5-6 fragment with 7-10 fragment, condensing 2-4 fragment with 5-10 fragment.

SYNTHESIS OF Lys—Hyp—Gly (2-4 fragment)

This synthesis is carried out as follows:

BOC—Lys—(Z)—Hyp—OMe
↓
BOC—Lys—(Z)—Hyp—OH
↓
BOC—Lys—(Z)—Hyp—Gly—OBu$^t$
↓
BOC—Lys—(Z)—Hyp—Gly—OH

This synthesis of 2-4 fragment is carried out as it has been described for the preparation of the same 2-4 fragment in the synthesis of octapeptide Lys—Hyp—Gly—Glu—Hyp—Gly—Pro—Lys.

SYNTHESIS OF Glu—Hyp—Gly—Pro—Lys—Gly (5-10 fragment)

This synthesis is carried out in two stages:
1. Synthesis of 5-6 fragment:
Z—Glu—(OBu$^t$)—Hyp—OH is obtained as it has been described in the preparation of the nonapeptide of formula (XV) (4).

2. Synthesis of 7-10 fragment:
The 7-10 fragment is obtained as follows:

Z—Gly—Pro + H—Lys—(BOC)—Gly—OBu$^t$
↓
Z—Gly—Pro—Lys—(BOC)—Gly—OBu$^t$
↓
H—Gly—Pro—Lys—(BOC)—Gly—OBu$^t$

Z—Gly—Pro—Lys—(BOC)—Gly—OBu$^t$ is obtained from Z—Gly—Pro and H—Lys—(BOC)—Gly—OBu$^t$ according to the same reaction as the one involved of the preparation of compound (X) (synthesis of nonapeptide of formula (XV) (4) in which Lys—(-BOC)—OBu$^t$ is replaced by Lys—(BOC)—Gly—OBu$^t$.

H—Gly—Pro—Lys—(BOC)—Gly—OBu$^t$ is obtained from Z—Gly—Pro—Lys—(BOC)—Gly—OBu$^t$ by hydrogenation.

The synthesis of 5-10 fragment is carried out as follows:
Z—Glu—(OBu$^t$)—Hyp—OH+H—Gly—Pro—Lys—(BOC)Gly—OBu$^t$→Z—Glu—(OBu$^t$)—Hyp—Gly—Pro—Lys—(BOC)—Gly—OBu$^t$→H—Glu—(OBu$^t$)—Hyp—Gly—Pro—Lys—(BOC)—Gly—OBu$^t$ Z—Glu—(OBu$^t$)—Hyp—Gly—Pro—Lys—(BOC)—Gly—OBu$^t$ is obtained by condensing Z—Glu—(OBu$^t$)—Hyp—OH on H—Gly—Pro—Lys—(-BOC)—Gly—OBu$^t$ in the same way as it has been described for the preparation of compound (XII) (in the synthesis of nonapeptide of formula (XV) (4).

H—Glu—(OBu$^t$)—Hyp—Gly—Pro—Lys—(BOC)—Gly—OBu$^t$ is obtained by hydrogenation in the same way as for the preparation of compound (XIII) obtained from compound (XII).

The nonapeptide is obtained as follows:
BOC—Lys—(Z)—Hyp—Gly—OH+H—Glu—(OBu$^t$)—Hyp—Gly—Pro—Lys—(BOC)—Gly—OBu$^t$→
BOC—Lys—(Z)—Hyp—Gly—Glu—(OBu$^t$)—Hyp—Gly—Pro—Lys—(BOC)—Gly—OBu$^t$→
Lys—Hyp—Gly—Glu—Hyp—Pro—Lys—Gly.

BOC—Lys—(Z)—Hyp—Gly—Glu—(OBu$^t$)—Hyp—Gly—Pro—Lys—(BOC)—Gly—OBu$^t$ is obtained by condensing 2-4 fragment on 5-10 fragment in the same way as it has been described for the preparation of compound (XIV) (in the synthesis of the nonapeptide of formula (XV) (4).

Lys—Hyp—Gly—Glu—Hyp—Gly—Pro—Lys—Gly is obtained from BOC—Lys—(Z-)—Hyp—Gly—Glu—(OBu$^t$)—Hyp—Gly—Pro—Lys—(BOC)—Gly—OBu$^t$ as it has been described in the preparation of the nonapeptide (XV) (4).

It must be pointed out that linking of the three contemplated fragments could have been carried out in other order without any problem.

In the synthesis of all the peptides, according to the invention, the hydroxy prolyl residue can be replaced by the prolyl residue, and the prolyl residue can be replaced by the hydroxy prolyl residue without modifying the synthesis.

By resorting to the preparation method described for the nonapeptide of formula (4), other peptides have been prepared among which the three following ones, hereunder identified, as examples:

Gly—Lys—Pro—Gly—Glu—Pro—Gly—Pro—Lys  (1)

$|\alpha|_D^{20} = -115°$ (c=0,5 H$_2$O)

| Gly-Lys-Pro-Gly-Glu-Pro-Gly-Pro-Lys (1) | | |
|---|---|---|
| $\|\alpha\|_D^{20} = -115°$ (c = 0,5 H$_2$O) | | |
| Elementary analysis: C$_{38}$H$_{63}$N$_{11}$O$_{12}$, 1,5 CH$_3$COOH, 3H$_2$O (1010) | | |
| C % | H % | N % |
| calculated 48.7 | 7.5 | 15.3 |
| found 48.7 | 7.2 | 15.3 |

| Lys-Hyp-Gly-Glu-Hyp-Gly-Pro-Lys-Gly (2) | | |
|---|---|---|
| $\|\alpha\|_D^{20} = -98.3°$ (c = 0.6 H$_2$O) | | |
| Elementary analysis: C$_{38}$H$_{63}$N$_{11}$O$_{12}$, 1,25 CH$_3$COOH, 4H$_2$O (1 045.14) | | |
| C % | H % | N % |
| calculated 46.5 | 7.3 | 14.7 |
| found 46.8 | 7.2 | 18.8 |

| Tyr-Gly-Lys-Hyp-Gly-Glu-Hyp-Gly-Pro-Lys (3) | | |
|---|---|---|
| $\|\alpha\|_D^{20} = -67.2°$ (c = 0.85 H$_2$O) | | |
| Elementary analysis: C$_{47}$H$_{70}$N$_{12}$O$_{16}$, 1.25 CH$_3$COOH, 6H$_2$O (1 242.36) | | |
| C % | H % | N % |
| calculated 47.8 | 7.0 | 13.5 |
| found 47.8 | 6.6 | 13.5 |

The peptides according to the invention, have been subjected to the following experiments, in the field of platelet aggregation, induced by type III collagen. The experiments which are described hereunder relate to the nonapeptides of formula (1), (2) and (4) and to the decapeptide of formula (3) of the invention.

STUDY OF PLATELET AGGREGATION INHIBITION

Method

The study of platelet aggregation is carried out under continuous stirring in an aggregometer known under the commercial designation LABINTEC, according to Born's method.

0.4 ml of citrated platelet (3.8%) rich plasma (PRP) are placed in the cuvette of the aggregometer. 0% of transmission is regulated with the PRP.

100% of transmission is regulated with a platelet poor plasma (PPP).

After the addition of 2.5 μg of type III polymerized collagen, the aggregation curve is drafted in which the optical transmission percentage value is plotted against the time. There is a phase corresponding to the time duration between the addition of collagen and the beginning of aggregation.

Two parameters are then deduced from the curve:

1. velocity (expressed in %, 30 seconds after the addition of the peptide to be tested):

it is calculated from the curve by measuring the distance on the "optical transmission percentage value" axis (in cm) between 0% transmission and 100% transmission (distance=x) and the distance (in cm) on the "time" axis between 0% transmission and the optical transmission value, 30 seconds after the beginning of aggregation (distance=y)

velocity = $(x-y)/x \cdot 100$ 2. intensity of the reaction (expressed in %):

it is calculated as for velocity, but in this case, y represents the value of optical transmission percentage, 2 minutes after the beginning of aggregation.

The percentage of inhibition of velocity and of inhibition of intensity are calculated as respect to the control test incubation of PRP in 10 μl of buffer solution, in which only type III collagen has been introduced.

EXPERIMENT I

400 μl of citrated (3.8%) platelet rich plasma pH 7.4 are incubated for five minutes, at 33° C., under constant stirring, respectively:

with 10 μl of 0.1M, Tris HCl buffer pH 7.4 (control experiment);

with 500 μg of peptide $\alpha_1$ (III)CB4 in 10 μl of the above mentioned buffer solution;

with increasing amounts of the nonapeptide of formula (4), in 10 μl of the above mentioned buffer solution (the increasing amounts are the following ones, expressed in n moles:

77
200
420
610
840

No aggregation of the platelets was noticed.

A minimal quantity (2.5 μg) of type III polymerized collagen inducing aggregation is added and the subsequent aggregation was recorded. The results relative to velocity (percent), velocity inhibition (percent), intensity, intensity inhibition (percent) are gathered in the following table I.

TABLE I

| Inducer of aggregation | Preincubations 0.4 ml of PRP + | Velocity % | % of inhibition of velocity | Insensity % | % of inhibition of intensity |
|---|---|---|---|---|---|
| Type III collagen 2.5 μg | 10 μl of buffer | 15.2 | | 62 | |
| | 10 μl GB4 | 9.8 | 35.5 | 37 | 40.5 |
| | nonapeptide (840 n moles) | 2.9 | 81 | 13.5 | 78 |
| | nonapeptide (610 n moles) | 1 | 93 | 4 | 93 |
| | nonapeptide (420 n moles) | 0 | 100 | 0 | 100 |
| | nonapeptide (200 n moles) | 2.1 | 86 | 6.5 | 88 |
| | nonapeptide (77 n moles) | 5.3 | 65 | 21 | 65 |

Another experiment has been carried out with the nonapeptide of formula (4), in the same conditions as for experiment I.

In this case, two different amounts of collagen have been used respectively for each amount of nonapeptide.

The results are gathered in the following table II.

TABLE II

| ACTIVITY OF THE NONAPEPTIDE OF FORMULA (4) AS REGARDS PLATELET AGGREGATION INDUCED BY TYPE III COLLAGEN | | | | | |
|---|---|---|---|---|---|
| Collagen type III (μg) | Nonapeptide n moles | Velocity % | % of inhibition of velocity | Intensity % | % of inhibition of intesity |
| 1.25 | 0 | 32 | | 90.9 | |
| 2.5 | | 34.3 | | 78.6 | |
| 1.25 | 25 | 0 | 100 | 0 | 100 |
| 2.5 | | untested | untested | untested | untested |
| 1.25 | 52 | 0 | 100 | 0 | 100 |
| 2.5 | | 35 | 0 | 78.6 | 0 |
| 1.25 | 105 | 0 | 100 | 0 | 100 |

TABLE II-continued

ACTIVITY OF THE NONAPEPTIDE OF FORMULA (4) AS REGARDS PLATELET AGGREGATION INDUCED BY TYPE III COLLAGEN

| Collagen type III (μg) | Nonapeptide n moles | Velocity % | % of inhibition of velocity | Intensity % | % of inhibition of intesity |
|---|---|---|---|---|---|
| 2.5 | | 34 | 0 | 74.5 | 5 |
| 1.25 | 210 | 2.1 | 90.9 | 2.9 | 96.8 |
| 2.5 | | 15.9 | 53.6 | 73 | 7.1 |
| 1.25 | 420 | 1.1 | 93.4 | 2.8 | 96.4 |
| 2.5 | | 4.2 | 88 | 16.6 | 78.8 |
| 1.25 | 840 | untested | untested | untested | untested |
| 2.5 | | 2.7 | 92 | 6.8 | 91 |

Figure 2:
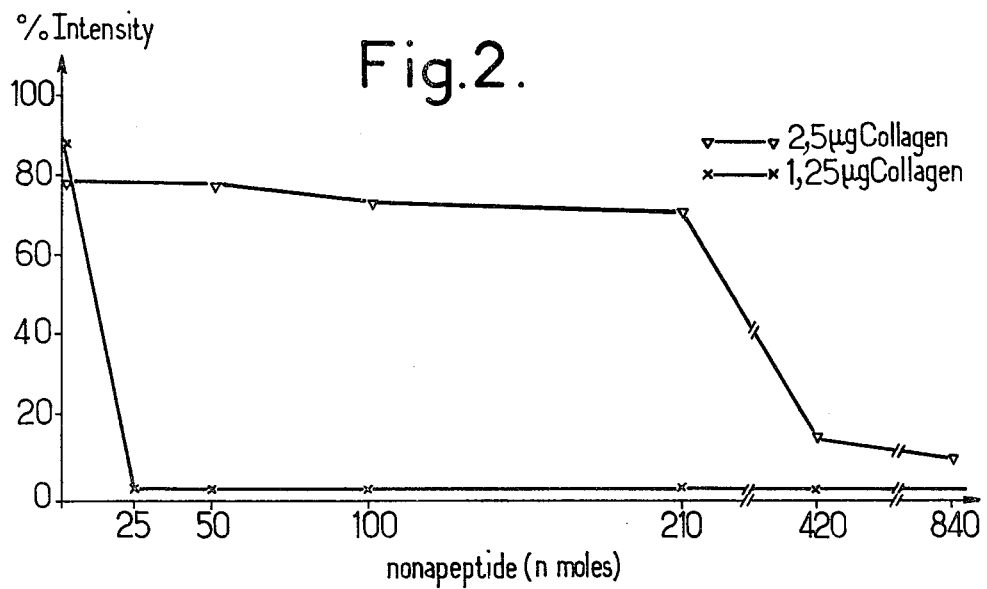

FIGS. 1 and 2 have been drafted accordingly, showing respectively:

the percentage of velocity plotted against the amount of nonapeptide (in n moles) for two respective amounts of collagen (2.5 μg and 1.25 μg);

the percentage of intensity plotted against the amount of nonapeptide (in n moles) for two respective amounts of collagen (2.5 μg and 1.25 μg).

The results show that the peptide of formula (4) presents a strong inhibitory effect on the aggregation of platelets induced by type III collagen. They also show that the concentration requested for inhibiting the aggregation induced by different amounts of collagen is dose-dependant on the nonapeptide.

One may also point out, from the table, that the nonapeptide of formula (4), in the concentration of 420 n moles is responsible for a total inhibition in platelet aggregation. A highly significant inhibition (65%) is observed for a concentration of 77 n moles.

The comparison between the results obtained with the three peptides (C2, HA4, T6), with respect to inhibition of platelet aggregation, shows that the small peptides according to the invention, are in our experiments as efficient as the bigger fragments (C2, HA4 and T6) in their ability to inhibit the platelet aggregation induced by type III collagen.

The peptides according to the invention inhibit aggregation induced only by collagen and collagen containing substances such as type III collagen.

Their specificity as regards the aggregation inducer has been experimented using platelet aggregation inducer such as:

arachidonic acid,
ionophore of the A 23 187 type, commercialized by Calbiochem. Behring.
ADP
thrombine in the amount of 0.1μ and 0.15μ

The results obtained for the nonapeptide of formula (4) are reported below in table III.

TABLE III

ACTIVITY OF THE NONAPEPTIDE OF FORMULA (4) AS REGARDS PLATELET AGGREGATION INDUCED BY ARACHIDONIC ACID IONOPHORE AND THROMBINE

| Inducer | Nonapeptide n moles | Velocity % | % of inhibition of velocity | Intensity % | % of inhibition of intensity |
|---|---|---|---|---|---|
| Arachidonic acid | 0 | 59.9 | | 81 | |
| 0.6 nM | 830 | 62.3 | 0 | 79.7 | 0 |
| Ionophore | 0 | 50 | | 81.2 | |
| 25 μM | 830 | 51.6 | 0 | 81.6 | 0 |
| ADP | 20 μl of buffer | 35.7 | | | |
| 10−6 M | 600 | 35.2 | 0 | | |
| Thrombine | 0 | 19.6 | | | |
| 0.1μ | 840 | 18.5 | | | |
| 0.15μ | 0 | 30.4 | | | |
| | 840 | 27.4 | | | |

From the results, it appears that the peptides according to the invention, do not inhibit aggregation induced by arachidonic acid, ionophore, ADP and thrombine.

EXPERIMENT III

Another experiment has been carried out with the nonapeptides of formula (1), (2) and (4) and the decapeptide of formula (3), in the same conditions as for experiment I.

A pentapeptide of formula:

Gly—Glu—Hyp—Gly—Pro has also been tested.

In this case, two different amounts of type III collagen (2 and 5 μg) have been used for different amounts of the above mentioned peptides, and the test with the pentapeptide has been carried out with 3 μg of type III collagen.

The results gathered in the following table IV, show that the peptides of formula (1), (2) and (3) inhibit platelet aggregation in the same way as the nonapeptide of formula (4). However, the pentapeptide tested has no activity with respect to aggregation of platelets induced by type III collagen.

TABLE IV

EFFECT OF THE DIFFERENT PEPTIDES (1), (2), (3) AND (4) ON PLATELET AGGREGATION

| Inducer | Nonapeptides (n moles) | Velocity % | % of inhibition of velocity | Intensity % | % of inhibition of intensity |
|---|---|---|---|---|---|
| Collagen 2 μg | 0 | 12.85 | — | 57.85 | — |
| | decapeptide (3) | | | | |
| | 840 | 0 | 100 | 0 | 100 |
| | 600 | 4.9 | 64 | 21.8 | 64.3 |
| | 420 | 7 | 48 | 33.8 | 44.6 |
| | nonapeptide (4) | 7.8 | 42.5 | 42.8 | 30 |
| Collagen 3 μg | 0 | 6.25 | — | 22.6 | — |
| | Gly—Glu—Hyp—Gly—Pro 840 (pH 7.4) | 6.95 | 0 | 24.7 | 0 |
| Collagen 5 μg | 0 | 11 | — | 40.7 | — |
| | nonapeptide (4) 840 | 5.39 | 51 | 22 | 46 |
| | nonapeptide (1) 840 | 5.6 | 49 | 24.6 | 47 |
| | nonapeptide (2) 840 | 5.1 | 53.6 | 20.4 | 50 |

STUDY OF PLATELET ACTIVATION INHIBITION

The peptides according to the invention inhibit aggregation of platelet induced by collagen without modifying the intracellular natural metabolism of the platelets, without involving cellular activation with the liberation of intraplatelet constituents.

A test has been carried out to study the inhibiting effect of the peptides according to the invention with respect to platelet activation induced by type III collagen.

The test has been carried out with the nonapeptide of formula (4) in which the release of endogenous serotonin contained in the platelet granules is studied.

The test consists of a pre-incubation in vitro of a platelet suspension in a physiological buffer (Tris: 0.35M, $Mg^+$: 1 mM; $K^+$: 2.5 mM; $Ca^{++}$: 2.5 mM; NaCl: 100 mM; glucose: 0.9%/ml; albumine: 3.5 mg/ml (reference: PATSCHEKE and WOMER, "Platelet activation detected by turbidometric shape change analysis. Differential influence of cytocholagin B and prostaglandin $E_1$". Thrombosis Research, vol. 12, 1978, p. 485).

The amount of platelets is of $1.2 \times 108$ platelets for 0.4 ml of buffer.

The pre-incubation is carried out in the presence of different nonapeptide concentrations, for 5 minutes, at a temperature of 37° C. The pre-incubation is followed by the addition of type III collagen, at the rate of 5 and 7 gammas. The incubation is carried out for 90 seconds and the behaviour of platelets with respect to aggregation is observed at the same time. The platelets are then centrifuged for 15 seconds in an EPPENDORF microcentrifuge. The supernatants are sampled and the release of endogenous serotonin is measured by the fluorometric method described in Thrombosis Research, vol. 10, 1977, p. 791-RAO, FRIEDLAND, GERRARD and WHITE "The influence of metaboliism on the assay of platelets", in a spectrophotometer commercialized by JOBIN & YVON under the designation JY3.

The results gathered in the following table V show the increasing inhibition of the release of serotonin induced by collagen corresponding to the increasing amounts of nonapeptide.

The inhibition is complete for a concentration of nonapeptides of 850 n moles.

The nonapeptide itself does not induce serotonin release.

The results relative to the study of aggregation which has been carried out in parallel assays, with the study of serotonin release, are also reported in table V.

The inhibition of serotonin release parallels the inhibition of aggregation, as measured by the velocity (%) after one minute.

TABLE V

INHIBITING EFFECT OF NONAPEPTIDE (4) ON SERONTONIN RELEASE

| Collagen | Nonapetides (n moles) | Velocity % after 1 mn | % of inhibition of velocity | Release % | % of inhibition of release |
|---|---|---|---|---|---|
| 0γ | 840 | 0 | — | 1.3 | — |
| 5γ | 0 | 17.4 | — | 49.8 | — |
| 5γ | 105 | 11.4 | 34 | 32.6 | 34 |
| 5γ | 210 | 8 | 54 | 27 | 46 |
| 5γ | 420 | 6.3 | 63.7 | 15.8 | 68 |
| 5γ | 840 | 0 | 100 | 3.4 | 93 |
| 7γ | 0 | 11 | — | 40 | — |
| 7γ | 210 | 17 | 0 | 34 | 15 |
| 7γ | 420 | 0 | 100 | 15.2 | 62 |
| 7γ | 840 | 0 | 100 | 7.9 | 80 |

STUDY OF THE NATURE OF THE FIXATION OF THE PEPTIDES OF THE INVENTION TO PLATELETS OR TO PLATELET MEMBRANES

The study of the nature of the interaction between type III collagen and platelets is carried out in the presence of tritiated (labelled) nonapeptide of formula:

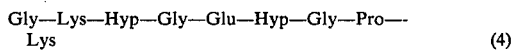

Gly—Lys—Hyp—Gly—Glu—Hyp—Gly—Pro—Lys        (4)

This study is carried out with complete platelets or membranes of the platelets.

1. Methods for tritiating the platelets or the platelet membranes

The complete platelets or the platelet membranes solubilized in triton (0.15%) are incubated in a physiological buffer of the type described above in the serotonin release test (in a total volume of 0.2 ml) at a temperature of 37° C. for 15 minutes. The incubation is carried out in presence of tritiated nonapeptide the specific activity of which is of 1 to 2 curie/n mole.

The nonapeptide fixed or linked to the platelet or to the membranes is separated from the free nonapeptide by filtration of the incubation medium through multiporous membranes having porosities of 0.8μ and 0.45μ respectively. The radio activity is directly determined on the filters and the percentage of linkages determined according to the following formula:

$$\% \text{ of linkages} = \frac{\text{radio-activity due to the platelets}}{\text{total radio-activity}} \times 100$$

Different characteristics of the linkage between the platelets or the platelet membranes and the peptides of the invention have been studied as explained below.

A specific linkage of a ligand to its specific receptor is substantially characterized by four properties:

the linkage percentage varies according to the protein concentration (of tables VI, X);
the linkage is liable to reach saturation (tables VII and XI);
the linkage is specific (table VIII);
the linkage is reversible (table IX) as evidenced by a dissociation of labelled ligand from the receptor as a function of time and in the presence of an excess of non labelled ligand.

(a) Tables VI and X respectively relate to the linkage (%) of the nonapeptide as a function of the protein concentration respectively for the platelet membranes and for the platelets.

It results from the study of tables VI and X that similar conclusions can be reached for the platelet membranes and for the complete platelets. In other words, the linkage percentage increases when the protein concentration increases. The linkage percentage is an increasing function of the number of receptors which are present in the incubation medium.

TABLE VI

LINKAGE (%) OF LABELLED (TRITIATED) NONAPEPTIDE (4) AS A FUNCTION OF THE PROTEIN CONCENTRATION (Platelet membranes)

| Nonapeptide H³ (ng) | Proteic concentration | | | | | | | |
|---|---|---|---|---|---|---|---|---|
| | 20 μg | 40 μg | 60 μg | 80 μg | 100 μg | 200 μg | 400 μg | 450 μg |
| 3 | 2.1% | 3.8% | 4.3% | 4.6% | 5.3% | — | — | — |
| 30 | 3.5% | 4.3% | 5% | 5.8% | 6.15% | 10.4% | 13% | 13.8% |

TABLE X

LINKAGE (%) OF THE NONAPEPTIDE AS A FUNCTION OF THE PLATELET CONCENTRATION (complete platelets)

| Nonapeptide | Platelet concentration | | | | |
|---|---|---|---|---|---|
| | 0.3 × 10⁸ | 0.6 × 10⁸ | 1.2 × 10⁸ | 2.4 × 10⁸ | 4.8 × 10⁸ |
| 20 μg | 2.35% | 3.85% | 5.1% | 7.8% | 10.4% |

(b) Tables VII an XI relate to the saturation and represent the variation of the linkage percentage as a function of the concentration of nonapeptide respectively for the platelet membranes and for the complete platelets. It results from the study of table VII, that the variation of the linkage percentage is linear up to a concentration of 12.5 ng of nonapeptide. Above this value of the concentration, the variation of the linkage percentages deeply decreases and nearly reaches a constant value.

From the study of table XI, it results that the saturation is complete from 1.2 ng of nonapeptide for a platelet concentration of $1.2 \times 10^8$ platelets in 0.2 ml of physiological buffer.

TABLE VII

LINKAGE (%) AS A FUNCTION OF THE LABELLED NONAPEPTIDE (4) (Platelet membranes)

| Nonapeptide H³ (ng) | Linkage (%) |
|---|---|
| 3 | 1.6 |
| 6 | 3.5 |
| 12 | 5.5 |
| 60 | 7.5 |
| 300 | 10.5 |

TABLE XI

LINKAGE SATURATION:LINKAGE (%) AS A FUNCTION OF THE NONAPEPTIDE (4) CONCENTRATION (Complete platelets)

| Platelet concentration | Nonapeptide concentration | | | | | | | |
|---|---|---|---|---|---|---|---|---|
| | 1.2 ng | 2.4 ng | 6 ng | 60 ng | 20 μg | 50 μg | 100 μg | 200 μg |
| 0.3 × 10⁸ | — | — | — | — | 2.35 | 2.5% | — | 3.1% |
| 0.6 × 10⁸ | — | — | — | — | 3.85% | 3% | 3% | 4% |
| 1.2 × 10⁸ | 5.1% | 5.6% | 4.8% | 5.5% | 5.1% | 6% | 5% | 5.1% |
| 4.8 × 10⁸ | — | — | — | — | 0.4% | — | 8% | 8% |

(c) Table VIII relates to the linkage specificity. It represents the linkage percentages between the platelet membranes and different peptides of the invention in the presence of various aggregation inducers (15 ng of peptide, 30 μg of platelet membrane).

The specificity of the linkage is assessed by the total displacement of the corresponding radio-activity by an excess of non labelled peptide of the invention. This excess corresponds to an amount of 100 to 1000 times more than the amount of non labelled peptide which is necessary to induce adhesion of the platelets.

Other platelet aggregation inducers interacting with the platelet membranes are not responsible for any displacement.

From table VIII, it is to be noted that the CB4 central fragment of collagen containing the nonapeptide of formula (4) is responsible for the displacement of the linkage of said nonapeptide.

TABLE VIII

SPECIFICITY OF THE LINKAGE (platelet membranes 30 μg)

| Nonapeptide H³ ng | Agent | Linkage % |
|---|---|---|
| 15 | 0 | 4 |

TABLE VIII-continued

SPECIFICITY OF THE LINKAGE
(platelet membranes 30 µg)

| Nonapeptide H³ ng | Agent | | Linkage % |
|---|---|---|---|
| | nonapeptide (4) | 15 µg | 0.26 |
| | | 150 µg | 0.7 |
| | nonapeptide (1) | 15 µg | 0 |
| | nonapeptide (2) | 15 µg | 0.4 |
| | nonapeptide (3) | 15 µg | 0.09 |
| | CB4 | 100 µg | 0.36 |
| | ADP | $10^{-2}$ M | 4.3 |
| | ionophore A 23 187 | 0.5 nM | 4.1 |
| | Adrenaline | 100 µg | 5.4 |
| | Arachidonic acid | 6 nM | 4.1 |

(d) Table IX relates to the study of the reversibility of the linkage of the nonapeptide of formula (4) to the platelets. Said reversibility results from the fact that the peptides according to the invention can be dissociated from the platelets as time goes on.

Said reversibility has been studied in the presence of two concentrations of labelled (nona)peptide which are respectively of 3 and 6 ng, for 30 µg of platelet membranes. After the binding of the labelled nonapeptide to the membranes, the incubation media are diluted to the 80 volumes:

in the absence of non labelled (nona)peptide;

and in the presence of an excess of non labelled (nona)peptide (as indicated under c) for the reversibility test).

The percentage of linkage is then determined as a function of an incubation duration ranging from 0 to 15 minutes.

The reversibility is measured by the dissociation factor and the dissociation time.

The results of table IX show a quick dissociation (measured by the semi-dissociation time). The semi-dissociation time which is of about 5 minutes, when there is no nonapeptide, is decreased to 2 minutes, when there is an excess of non labelled nonapeptide, which corresponds to an increase of the dissociation.

TABLE IX

REVERSIBILITY OF THE LINKAGE
(Platelet membranes)

| Nona-peptide H³ | Dissociation factor | Dissociation time | | | | |
|---|---|---|---|---|---|---|
| | | 0' | 2' | 5' | 10' | 15' |
| 3 ng | dilution 1/80 | 3.2% | 1.75% | 1.55% | 1% | 0.6% |
| | dilution 1/80 + 100 µg of nonapeptide | 3.2% | 1% | — | 0.5% | 0.1% |
| 6 ng | dilution 1/80 | 5.9% | 4.8% | 3% | 2.4% | 1.5% |
| | dilution 1/80 + 100 µg of nonapeptide | 5.9% | 3% | — | 1.5% | 1% |

The peptides according to the invention, notably the following peptides:

Tyr—Gly—Lys—Hyp—Gly—Glu—Hyp—Gly—Pro—Lys

Tyr—Gly—Lys—Hyp—Gly—Hyp—Glu—Gly—Pro—Lys     (3)

can be used as tracers, particularly if labelled radioactively.

The peptides according to the invention can be used as identifying means of the particular sites of platelets that are involved in the interaction between the latter and type III collagen.

More particularly, they can be used as a means of discriminating the sites involved in platelet adhesion and for aggregation induced by type III collagen from the other sites possibly involved in platelet adhesion induced by other inducers or more generally of selectively preventing adhesion of platelets liable of being induced by collagen in experimental induction assays in the presence of would-be inducers or mixtures of inducers of platelet adhesion and/or aggregation.

One must point out that the peptides according to the invention, can also be used with any type of collagen such as type I, IV and V, as well as with microfibrils or substances containing any type of collagen.

The peptides according to the invention because of their interesting pharmacological properties of antiaggregation can also be the active principle, the control of coagulation, particularly for preventing the formation of thrombosis in men whose blood is in hypercoagulable state.

The compositions containing a dose of any of such peptides effective to prevent interaction in vivo between collagen and platelets can be administered by intravenous, intramuscular or subcutaneous route, in the form of a solution pharmaceutically acceptable and in sterile vehicle.

The peptides according to the invention can also be administered by oral, sublingual or nasal route, when associated with solid or liquid pharmaceutically acceptable excipient.

They can also be administered by rectal route when associated to excipients suitable accordingly. They can also be administered in the form of liposomes.

As is self-evident and as emerges besides already from the foregoing, the invention is in no way limited to the embodiments which have been more particularly envisaged; it encompasses, on the contrary:

We claim:

1. A peptide of the formula:

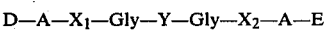
    D—A—X₁—Gly—Y—Gly—X₂—A—E wherein:

D is a member selected from the group consisting of H, Gly and Tyr—Gly;

E is a member selected from the group consisting of OH and Gly;

X₁ and X₂ are the same or different and each is an aminoacyl residue selected from the group consisting of hydroxyprolyl and prolyl;

Y is a residue selected from the group consisting of —Z—X₃— and —X₃—Z— wherein X₃ is hydroxyprolyl or prolyl, and Z is a spacer aminoacyl residue selected from among glutaminyl, glutamyl, aspartyl, asparginyl and alanyl residues, and A is selected from among arginyl, ornithyl, lysyl or hydroxylysyl residues.

2. A peptide comprising amino acids, which, except glycyl, are all levorotatory, of the formula:

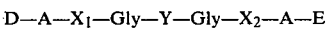
    D—A—X₁—Gly—Y—Gly—X₂—A—E wherein:

D is a member selected from the group consisting of H, Gly and Tyr—Gly;

E is a member selected from the group consisting of OH and Gly;

$X_1$ and $X_2$ represent, independently from each other, either a hydroxyprolyl or a prolyl residue;

Y represents either a $-Z-X_3-$ or a $-X_3-Z-$ residue, wherein $X_3$ is a hydroxyprolyl or prolyl residue, and Z is a spacer aminoacyl residue selected from among glutaminyl, glutamyl, aspartyl, asparaginyl and alanyl residues; and A is selected from among arginyl, ornithyl or lysyl residues.

3. Peptide according to claim 2, characterized by the fact that A is lysyl.

4. The peptides of the following formula:

Lys—Pro—Gly—Glu—Pro—Gly—Pro—Lys
Lys—Hyp—Gly—Glu—Pro—Gly—Hyp—Lys
Lys—Pro—Gly—Glu—Pro—Gly—Hyp—Lys
Lys—Hyp—Gly—Glu—Pro—Gly—Pro—Lys
Lys—Pro—Gly—Glu—Hyp—Gly—Pro—Lys
Lys—Hyp—Gly—Glu—Hyp—Gly—Hyp—Lys
Lys—Pro—Gly—Glu—Hyp—Gly—Hyp—Lys
Lys—Hyp—Gly—Glu—Hyp—Gly—Pro—Lys
Gly—Lys—Pro—Gly—Glu—Pro—Gly—Pro—Lys
Gly—Lys—Hyp—Gly—Glu—Pro—Gly—Hyp—Lys
Gly—Lys—Pro—Gly—Glu—Pro—Gly—Hyp—Lys
Gly—Lys—Hyp—Gly—Glu—Pro—Gly—Pro—Lys
Gly—Lys—Pro—Gly—Glu—Hyp—Gly—Pro—Lys
Tyr—Gly—Lys—Hyp—Gly—Glu—Hyp—Gly—Pro—Lys
Lys—Pro—Gly—Pro—Glu—Gly—Pro—Lys
Lys—Hyp—Gly—Pro—Glu—Gly—Hyp—Lys
Lys—Pro—Gly—Pro—Glu—Gly—Hyp—Lys
Lys—Hyp—Gly—Pro—Glu—Gly—Pro—Lys
Lys—Pro—Gly—Hyp—Glu—Gly—Pro—Lys
Lys—Hyp—Gly—Hyp—Glu—Gly—Hyp—Lys
Lys—Pro—Gly—Hyp—Glu—Gly—Hyp—Lys
Lys—Hyp—Gly—Hyp—Glu—Gly—Pro—Lys
Gly—Lys—Pro—Gly—Pro—Glu—Gly—Pro—Lys
Gly—Lys—Hyp—Gly—Pro—Glu—Gly—Hyp—Lys
Gly—Lys—Pro—Gly—Pro—Glu—Gly—Hyp—Lys
Gly—Lys—Hyp—Gly—Pro—Glu—Gly—Pro—Lys
Gly—Lys—Pro—Gly—Hyp—Glu—Gly—Pro—Lys
Gly—Lys—Hyp—Gly—Glu—Hyp—Gly—Hyp—Lys
Gly—Lys—Pro—Gly—Glu—Hyp—Gly—Hyp—Lys
Gly—Lys—Hyp—Gly—Glu—Hyp—Gly—Pro—Lys
Lys—Pro—Gly—Glu—Pro—Gly—Pro—Lys—Gly
Lys—Hyp—Gly—Glu—Pro—Gly—Hyp—Lys—Gly
Lys—Pro—Gly—Glu—Pro—Gly—Hyp—Lys—Gly
Lys—Hyp—Gly—Glu—Pro—Gly—Pro—Lys—Gly
Lys—Pro—Gly—Glu—Hyp—Gly—Pro—Lys—Gly
Lys—Hyp—Gly—Glu—Hyp—Gly—Hyp—Lys—Gly
Lys—Pro—Gly—Glu—Hyp—Gly—Hyp—Lys—Gly
Lys—Hyp—Gly—Glu—Hyp—Gly—Pro—Lys—Gly
Tyr—Gly—Lys—Hyp—Gly—Glu—Hyp—Gly—Pro—Lys
Lys—Pro—Gly—Pro—Glu—Gly—Pro—Lys
Lys—Hyp—Gly—Pro—Glu—Gly—Hyp—Lys
Lys—Pro—Gly—Pro—Glu—Gly—Hyp—Lys
Lys—Pro—Gly—Hyp—Glu—Gly—Pro—Lys
Lys—Hyp—Gly—Hyp—Glu—Gly—Hyp—Lys
Lys—Pro—Gly—Hyp—Glu—Gly—Hyp—Lys
Lys—Hyp—Gly—Hyp—Glu—Gly—Pro—Lys
Gly—Lys—Pro—Gly—Pro—Glu—Gly—Pro—Lys
Gly—Lys—hyp—Gly—Pro—Glu—Gly—Hyp—Lys
Gly—Lys—Pro—Gly—Pro—Glu—Gly—Hyp—Lys
Gly—Lys—Hyp—Gly—Pro—Glu—Gly—Pro—Lys
Gly—Lys—Pro—Gly—Hyp—Glu—Gly—Pro—Lys
Gly—Lys—hyp—Gly—Hyp—Glu—Gly—Hyp—Lys
Gly—Lys—Pro—Gly—Hyp—Glu—Gly—Hyp—Lys
Gly—Lys—Hyp—Gly—Hyp—Glu—Gly—Pro—Lys
Lys—Pro—Gly—Pro—Glu—Gly—Pro—Lys—Gly
Lys—Hyp—Gly—Pro—Glu—Gly—Hyp—Lys—Gly
Lys—Pro—Gly—Pro—Glu—Gly—Hyp—Lys—Gly
Lys—Hyp—Gly—Pro—Glu—Gly—Pro—Lys—Gly
Lys—Pro—Gly—Hyp—Glu—Gly—Pro—Lys—Gly
Lys—Hyp—Gly—Hyp—Glu—Gly—Hyp—Lys—Gly
Lys—Pro—Gly—Hyp—Glu—Gly—Hyp—Lys—Gly
Lys—Hyp—Gly—Hyp—Glu—Gly—Pro—Lys—Gly
Tyr—Gly—Lys—Hyp—Gly—Glu—Hyp—Gly—Pro—Lys.

5. Peptide according to claim 2, of the formula:

$$D-A-X_1-Gly-2-X_3-Gly-X_2-A-E$$

in which:

D is a member selected from the group consisting of H, Gly and Tyr—Gly;

E is a member selected from the group consisting of OH and Gly;

A represents a residue chosed from the following: lysyl, arginyl;

$X_1$, $X_2$ and $X_3$ represent independently from each other either the hydroxyprolyl residue, or the prolyl residue; Z is selected from among glutaminyl, glutamyl, aspartyl, asparaginyl and alanyl residues.

6. Peptide according to claim 2, of the formula:

$$D-A-X_1-Gly-X_3-Z-Gly-X_2-A-E$$

in which:

D is a member selected from the group consisting of H, Gly and Tyr—Gly;

E is a member selected from the group consisting of OH and Gly;

A represents a residue chosen from the following: lysyl, arginyl;

$X_1$, $X_2$ and $X_3$ represent independently from each other either the hydroxyprolyl residue, or the prolyl residue;

Z is selected from among glutaminyl, glutamyl, aspartyl, asparaginyl and alanyl residues.

7. Peptide according to claim 2, wherein Z represents the glutamyl residue, A represents a residue chosen from the following: lysyl, arginyl, the formulae of the corresponding peptides then comprising either of the following:

$$D-A-X_1-gly-Glu-X_3-Gly-X_2-A-E$$

$$D-A-X_1-Gly-X_3-Glu-Gly-X_2-A-E$$

8. Peptide according to claim 2, wherein A represents the lysyl residue, and Z represents a glutamyl residue, the formulae of the corresponding peptides then comprising:

$$D-Lys-X_1-Gly-Glu-X_3-Gly-X_2-Lys-E$$

$$D-Lys-X_1-Gly-X_3-Glu-Gly-X_2-Lys-E$$

in which:

D is a member selected from the group consisting of H, Gly and Tyr—Gly;

E is a member selected from the group consisting of OH and Gly;

$X_1$, $X_2$ and $X_3$ represent independently from each other either the hydroxyprolyl residue, or the prolyl residue.

9. A pharmaceutical composition, particularly for preventing platelet aggregation, comprising in association with a pharmaceutical vehicle, a dose of a peptide according to any of claims 1, 2, 3, 5, 6, 7 or 8 effective to prevent interaction in vivo between collagen and platelets.

10. A pharmaceutical composition, particularly for preventing platelet aggregation, comprising in association with a pharmaceutical vehicle, an effective dose of at least one of the peptides of the following formula:

Lys—Pro—Gly—Glu—Pro—Gly—Pro—Lys
Lys—Hyp—Gly—Glu—Pro—Gly—Hyp—Lys
Lys—Pro—Gly—Glu—Pro—Gly—Hyp—Lys
Lys—Hyp—Gly—Glu—Pro—Gly—Pro—Lys
Lys—Pro—Gly—Glu—Hyp—Gly—Pro—Lys
Lys—Hyp—Gly—Glu—Hyp—Gly—Hyp—Lys
Lys—Pro—Gly—Glu—Hyp—Gly—Hyp—Lys
Lys—Hyp—Gly—Glu—Hyp—Gly—Pro—Lys
Gly—Lys—Pro—Gly—Glu—Pro—Gly—Pro—Lys
Gly—Lys—Hyp—Gly—Glu—Pro—Gly—Hyp—Lys
Gly—Lys—Pro—Gly—Glu—Pro—Gly—Hyp—Lys
Gly—Lys—Hyp—Gly—Glu—Pro—Gly—Pro—Lys
Gly—Lys—Pro—Gly—Glu—Hyp—Gly—Pro—Lys
Tyr—Gly—Lys—Hyp—Gly—Glu—Hyp—Gly—Pro—Lys
Lys—Pro—Gly—Pro—Glu—Gly—Pro—Lys
Lys—Hyp—Gly—Pro—Glu—Gly—Hyp—Lys
Lys—Pro—Gly—Pro—Glu—Gly—Hyp—Lys
Lys—Hyp—Gly—Pro—Glu—Gly—Pro—Lys
Lys—Pro—Gly—Hyp—Glu—Gly—Pro—Lys
Lys—Hyp—Gly—Hyp—Glu—Gly—Hyp—Lys
Lys—Pro—Gly—Hyp—Glu—Gly—Hyp—Lys
Lys—Hyp—Gly—Hyp—Glu—Gly—Pro—Lys
Gly—Lys—Pro—Gly—Pro—Glu—Gly—Pro—Lys
Gly—Lys—Hyp—Gly—Pro—Glu—Gly—Hyp—Lys
Gly—Lys—Pro—Gly—Pro—Glu—Gly—Hyp—Lys
Gly—Lys—Hyp—Gly—Pro—Glu—Gly—Pro—Lys
Gly—Lys—Pro—Gly—Hyp—Glu—Gly—Pro—Lys
Gly—Lys—Hyp—Gly—Hyp—Glu—Gly—Hyp—Lys
Gly—Lys—Pro—Gly—Glu—Hyp—Gly—Hyp—Lys
Gly—Lys—Hyp—Gly—Glu—Hyp—Gly—Pro—Lys
Lys—Pro—Gly—Glu—Pro—Gly—Pro—Lys—Gly
Lys—Hyp—Gly—Glu—Pro—Gly—Hyp—Lys—Gly
Lys—Pro—Gly—Glu—Pro—Gly—Hyp—Lys—Gly
Lys—Hyp—Gly—Glu—Pro—Gly—Pro—Lys—Gly
Lys—Pro—Gly—Glu—Hyp—Gly—Pro—Lys—Gly
Lys—Hyp—Gly—Glu—Hyp—Gly—Hyp—Lys—Gly
Lys—Pro—Gly—Glu—Hyp—Gly—Hyp—Lys—Gly
Lys—Hyp—Gly—Glu—Hyp—Gly—Pro—Lys—Gly
Tyr—Gly—Lys—Hyp—Gly—Glu—Hyp—Gly—Pro—Lys
Lys—Pro—Gly—Pro—Glu—Gly—Pro—Lys
Lys—Hyp—Gly—Pro—Glu—Gly—Hyp—Lys
Lys—Pro—Gly—Pro—Glu—Gly—Hyp—Lys
Lys—Hyp—Gly—Pro—Glu—Gly—Pro—Lys
Lys—Pro—Gly—Hyp—Glu—Gly—Pro—Lys
Lys—Hyp—Gly—Hyp—Glu—Gly—Hyp—Lys
Lys—Pro—Gly—Hyp—Glu—Gly—Hyp—Lys
Lys—Hyp—Gly—Hyp—Glu—Gly—Pro—Lys
Gly—Lys—Pro—Gly—Pro—Glu—Gly—Pro—Lys
Gly—Lys—Hyp—Gly—Pro—Glu—Gly—Hyp—Lys
Gly—Lys—Pro—Gly—Pro—Glu—Gly—Hyp—Lys
Gly—Lys—Hyp—Gly—Pro—Glu—Gly—Pro—Lys
Gly—Lys—Pro—Gly—Hyp—Glu—Gly—Pro—Lys
Gly—Lys—Hyp—Gly—Hyp—Glu—Gly—Hyp—Lys
Gly—Lys—Pro—Gly—Hyp—Glu—Gly—Hyp—Lys
Gly—Lys—Hyp—Gly—Hyp—Glu—Gly—Pro—Lys
Lys—Pro—Gly—Pro—Glu—Gly—Pro—Lys—Gly
Lys—Hyp—Gly—Pro—Glu—Gly—Hyp—Lys—Gly
Lys—Pro—Gly—Pro—Glu—Gly—Hyp—Lys—Gly
Lys—Hyp—Gly—Pro—Glu—Gly—Pro—Lys—Gly
Lys—Pro—Gly—Hyp—Glu—Gly—Pro—Lys—Gly
Lys—Hyp—Gly—Hyp—Glu—Gly—Hyp—Lys—Gly
Lys—Pro—Gly—Hyp—Glu—Gly—Hyp—Lys—Gly
Lys—Hyp—Gly—Hyp—Glu—Gly—Pro—Lys—Gly
Tyr—Gly—Lys—Hyp—Gly—Hyp—Glu—Gly—Pro—Lys.

11. A method of preventing platelet aggregation in a host, which comprises administering to said host an effective amount of a peptide of any one of claims 1, 2, 3, 5, 6, 7, or 8 and a pharmaceutically acceptable vehicle.